(12) United States Patent  
Richard

(10) Patent No.: US 7,439,380 B2  
(45) Date of Patent: Oct. 21, 2008

(54) DIARYLBUTADIENE-SUBSTITUTED DIORGANOPOLYSILOXANES AND PHOTOPROTECTIVE COMPOSITIONS COMPRISED THEREOF

(75) Inventor: Herve Richard, Villepinte (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 11/798,026

(22) Filed: May 9, 2007

(65) Prior Publication Data

US 2007/0213548 A1 Sep. 13, 2007

Related U.S. Application Data

(62) Division of application No. 10/995,226, filed on Nov. 24, 2004, now Pat. No. 7,229,610.

(60) Provisional application No. 60/526,987, filed on Dec. 5, 2003.

(30) Foreign Application Priority Data

Nov. 25, 2003 (FR) .................................. 03 50900

(51) Int. Cl.  
  *C07F 7/04* (2006.01)
(52) U.S. Cl. ..................................................... 556/419
(58) Field of Classification Search ........................ None  
  See application file for complete search history.

(56) References Cited

U.S. PATENT DOCUMENTS 6,004,540 A 12/1999 Richard et al.  
2005/0201957 A1 9/2005 Richard

FOREIGN PATENT DOCUMENTS

| EP | 0 712 855 A1 | 5/1996 |
| EP | 0 845 466 A1 | 6/1998 |
| JP | 2002-53527 A | 2/2002 |
| WO | 03/027168 A1 | 4/2003 |

*Primary Examiner*—Samuel A Barts  
(74) *Attorney, Agent, or Firm*—Buchanan, Ingersoll & Rooney, PC

(57) ABSTRACT

Novel 4,4-diarylbutadiene-substituted diorganopolysiloxanes having the structural formulae (1) or (2):

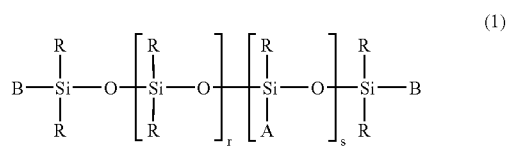

(1)

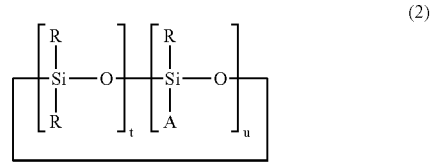

(2)

in which A is a radical of formula (3) below:

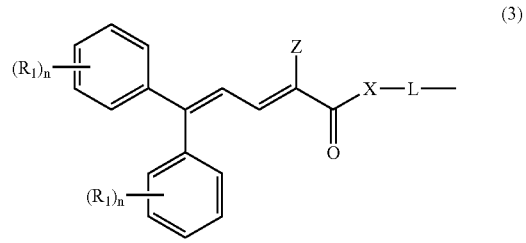

(3)

are useful sunscreens for UV-photoprotecting human skin against the damaging effects of UV-radiation, notably UV-A radiation.

27 Claims, No Drawings

DIARYLBUTADIENE-SUBSTITUTED DIORGANOPOLYSILOXANES AND PHOTOPROTECTIVE COMPOSITIONS COMPRISED THEREOF

CROSS-REFERENCE TO PRIORITY/PROVISIONAL APPLICATIONS

This application is a divisional of application Ser. No. 10/995,226, filed Nov. 24, 2004 now U.S. Pat. No. 7,229 610, which is hereby expressly incorporated by reference in its entirety.

This application claims priority under 35U.S.C. §119 of FR 03/50900, filed Nov. 25, 2003, and of provisional application Ser. No. 60/526,987, filed Dec., 20003, each hereby expressly incorporated by reference and each assigned to the assignee hereof. This application is also a continuation of said '987 provisional.

BACKGROUND OF THE INVENTION

1. Technical Field of the Invention

The present invention relates to novel diorganosiloxane compounds containing a 4,4-diarylbutadiene functional group.

The present invention also relates to the formulation of these diorganosiloxane compounds containing a 4,4-diarylbutadiene function into cosmetic compositions useful for screening out UV-A radiation.

This invention also relates to photoprotective compositions comprising diorganosiloxane compounds containing a 4,4-diarylbutadiene function, as sunscreens that are active in the field of UV radiation and more particularly in the field of UV-A rays.

2. Description of Background and/or Related and/or Prior Art

It is known that radiation with wavelengths of from 280 nm to 400 nm permits tanning of the human epidermis and that radiation with wavelengths of from 280 to 320 nm, which is known as UV-B radiation, causes skin burns and erythema that may be harmful to the development of a natural tan. For these reasons and also for aesthetic reasons, there is increasing demand for means for controlling this natural tanning. This UV-B radiation should thus be screened out.

It is also known that UV-A rays, with wavelengths of between 320 and 400 nm, which cause browning of the skin, are liable to induce impairment in the skin, especially in the case of sensitive skin and/or skin that is continually exposed to sunlight. UV-A rays in particular result in a loss of elasticity of the skin and the appearance of wrinkles, leading to premature aging of the skin. They promote triggering of the erythemal reaction or amplify this reaction in the case of certain individuals and may even be the cause of phototoxic or photoallergic reactions. Thus, for aesthetic and cosmetic reasons such as the conservation of the natural elasticity of the skin, more and more individuals wish to control the effect of UV-A rays on their skin. It is thus desirable also to screen out UV-A radiation.

There is at the present time an ever increasing need for aromatic compounds that are effective at screening out UV-A radiation and preferably in the range from 340 to 400 nm (range known as long UV-A or UV-A-I). Besides their good photoprotective efficacy in this range, the desired UV-A screening agents should have good cosmetic properties, good solubility in the usual solvents and in particular in fatty substances such as oils and fats, good resistance to water and to perspiration (remanence) and also satisfactory photostability.

A limited number of organic compounds that are effective towards UV-A rays and especially long UV-A rays are currently available on the UV-screening agent market.

In this regard, one family of UV-A screening agents that is particularly effective in the UV-A range currently includes dibenzoylmethane derivatives, and especially 4-tert-butyl-4'-methoxydibenzoylmethane, which specifically have good intrinsic absorbing power. These dibenzoylmethane derivatives, which are now products that are well known per se as screening agents active in the UV-A range, are described especially in FR-A-2,326,405 and FR-A-2,440,933, and also in EP-A-0-114,607; 4-tert-butyl-4'-methoxydibenzoylmethane is moreover currently sold under the trademark "Parsol 1789" by Hoffmann LaRoche.

Unfortunately, it transpires that dibenzoylmethane derivatives are products that are relatively photosensitive to UV-A radiation, i.e., more specifically, they have an annoying tendency to be degraded more or less quickly by the action of this radiation. Thus, this substantial lack of photochemical stability of dibenzoylmethane derivatives with respect to ultraviolet radiation, to which they are by nature intended to be subjected, does not make it possible to ensure constant protection during prolonged exposure to the sun, and as a result the user needs to make repeated applications at regular and short intervals in order to obtain effective protection of the skin against UV rays.

Another difficulty, which is independent of the one mentioned above, encountered with dibenzoylmethane derivatives is that they are lipophilic screening agents that have the particular feature but also the drawback of being solid at room temperature. As a result, their use in an antisun or sunscreen cosmetic composition entails certain constraints as regards their formulation and application, in particular when it is a matter of finding solvents for dissolving them correctly, alone or in combination with other screening agents.

Thus, need continues to exist for novel families of aromatic compounds that are effective in terms of screening in the UV-A range and especially the long UV-A range, but which are photostable and also have good solubility in the usual solvents, good cosmetic properties and also good resistance to water and to perspiration (remanence).

SUMMARY OF THE INVENTION

Surprisingly, a novel family of diorganosiloxane compounds containing a 4,4-diarylbutadiene functional group has now been developed which ameliorates or avoids the above disadvantages and drawbacks of the prior art.

The present invention thus features a novel family of diorganosiloxane compounds containing a 4,4-diarylbutadiene function of general formula (1) or (2) more fully described hereinbelow.

This invention also features the formulation of at least one diorganosiloxane compound containing a 4,4-diarylbutadiene function of general formula (1) or (2) into cosmetic or dermatological compositions useful for screening out rays with wavelengths of from 320 to 400 nm.

The present invention accordingly features photoprotective compositions comprising at least one diorganosiloxane compound containing a 4,4-diarylbutadiene function of general formula (1) or (2) more fully described hereinbelow.

The diorganosiloxane compounds containing a 4,4-diarylbutadiene function, in accordance with the invention, are in isolated form or in the form of a mixture and correspond to one of the general formulae (1) or (2) below:

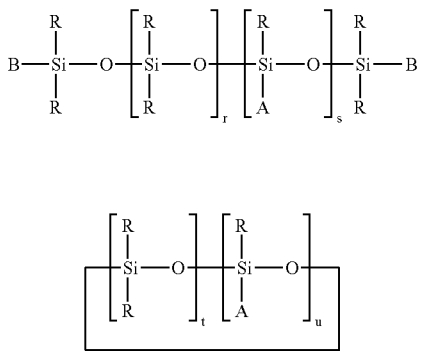
(1)

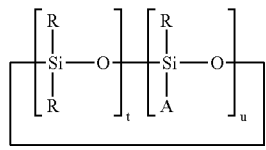
(2)

in which A is a radical of formula (3) below:

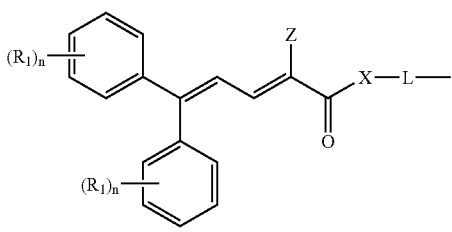
(3)

in which the radicals $R_1$, which may be identical or different, are each a hydroxyl radical, a saturated or unsaturated, linear or branched $C_1$-$C_{10}$ alkyl radical, a saturated or unsaturated, linear or branched $C_1$-$C_{10}$ alkoxy radical, with the proviso that two adjacent groups $R_1$ may together form a $C_1$-$C_3$ alkylenedioxy ring; $\underline{n}$ is an integer ranging from 0 to 2; the radical Z is hydrogen, —(C=O)OR$_2$, —(C=O)R$_3$, —(C=O)NR$_4$R$_5$, —SO$_2$R$_6$, —CN or —(C=O)—X-L; X is —O— or —NR$_4$—; L is a divalent radical attaching the radical A to the silicone chain and corresponding to one of the formulae (a), (a') or (a") below:

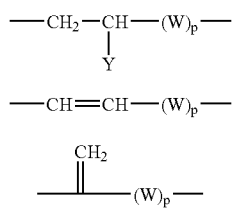
(a)
(a')
(a")

in which W is a saturated or unsaturated, linear or branched $C_1$-$C_6$ alkylene radical, optionally substituted with a hydroxyl radical or a saturated or unsaturated, linear or branched $C_1$-$C_8$ alkyl radical; Y is a hydrogen atom, a hydroxyl radical or a saturated or unsaturated, linear or branched $C_1$-$C_8$ alkyl radical; $\underline{p}$ is 0 or 1; the radicals R, which may be identical or different, are each a saturated or unsaturated, linear or branched $C_1$-$C_{20}$ alkyl radical, a phenyl radical, a 3,3,3-trifluoropropyl radical or a trimethylsilyloxy radical, at least 80% in numerical terms of the radicals R being methyl radicals; the radicals B, which may be identical or different, are each a radical R or a radical A; $\underline{r}$ is a number ranging from 0 to 50; $\underline{s}$ is a number ranging from 0 to 20 and, if $\underline{s}$ is 0, at least one of the two radicals B is a radical A; $\underline{u}$ is a number ranging from 1 to 6 inclusive; $\underline{t}$ is a number ranging from 0 to 10; $\underline{t+u}$ is greater than or equal to 3; the radical $R_2$ is hydrogen or a saturated or unsaturated, linear or branched $C_1$-$C_{20}$ alkyl radical; the radical $R_3$ is a saturated or unsaturated, linear or branched $C_1$-$C_{20}$ alkyl radical or a $C_6$-$C_{12}$ aryl radical; the radicals $R_4$ and $R_5$, which may be identical or different, are each hydrogen or a saturated or unsaturated, linear or branched $C_1$-$C_{20}$ alkyl radical; and the radical $R_6$ is a saturated or unsaturated, linear or branched $C_1$-$C_{20}$ alkyl radical or a $C_6$-$C_{12}$ aryl radical, with the proviso that when two groups (C=O)—X-L- are present, L is bonded to only one group A or B of formula (1) or (2): i.e., $\underline{s}$=1 with B being other than A or $\underline{s}$=0 and only one B is A for formula (1) and $\underline{u}$=1 for formula (2).

DETAILED DESCRIPTION OF BEST MODE AND SPECIFIC/PREFERRED EMBODIMENTS OF THE INVENTION

Although, in formula (3) above, only the isomers in which the substituent Z is in the cis position relative to the diaryl substituent are represented, this formula should be understood as also including the corresponding trans isomer.

In formulae (1) and (2) above, the alkyl radicals may be linear or branched, saturated or unsaturated and selected especially from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The alkyl radical that is particularly preferred is the methyl radical.

In formula (3) above, the alkoxy radicals may be linear or branched and selected especially from among methoxy, ethoxy, n-propoxy, isopropoxy, n-butoxy and isobutoxy radicals. The alkoxy radical that is particularly preferred is the methoxy radical.

In formula (1) above, the aryl radicals are preferably phenyl.

The linear or cyclic diorganosiloxanes of formula (1) or (2) within the scope of the present invention are oligomers or random polymers preferably satisfying at least one, and even more preferably all, of the following characteristics:

the radical Z is —(C=O)R$_3$, —CN or —(C=O)—X-L-;

$R_3$ is a $C_1$-$C_4$ alkyl radical and even more preferably ethyl;

R is $C_1$-$C_4$ alkyl and even more preferably methyl;

B is $C_1$-$C_4$ alkyl and even more preferably methyl (in the case where the compound is of formula (1));

$\underline{r}$ ranges from 0 to 10 inclusive; $\underline{s}$ ranges from 0 to 6 inclusive (in the case where the compound is of formula (1));

$\underline{t+u}$ ranges from 3 to 5 (in the case where the compound is of formula (2));

$\underline{n}$ is 0;

W is CH$_2$;

$\underline{p}$ is 1;

Y is H or CH$_3$.

Among the preferred diorganosiloxanes of formula (1), the compounds A, B, C, D and E having the following formulae are representative:

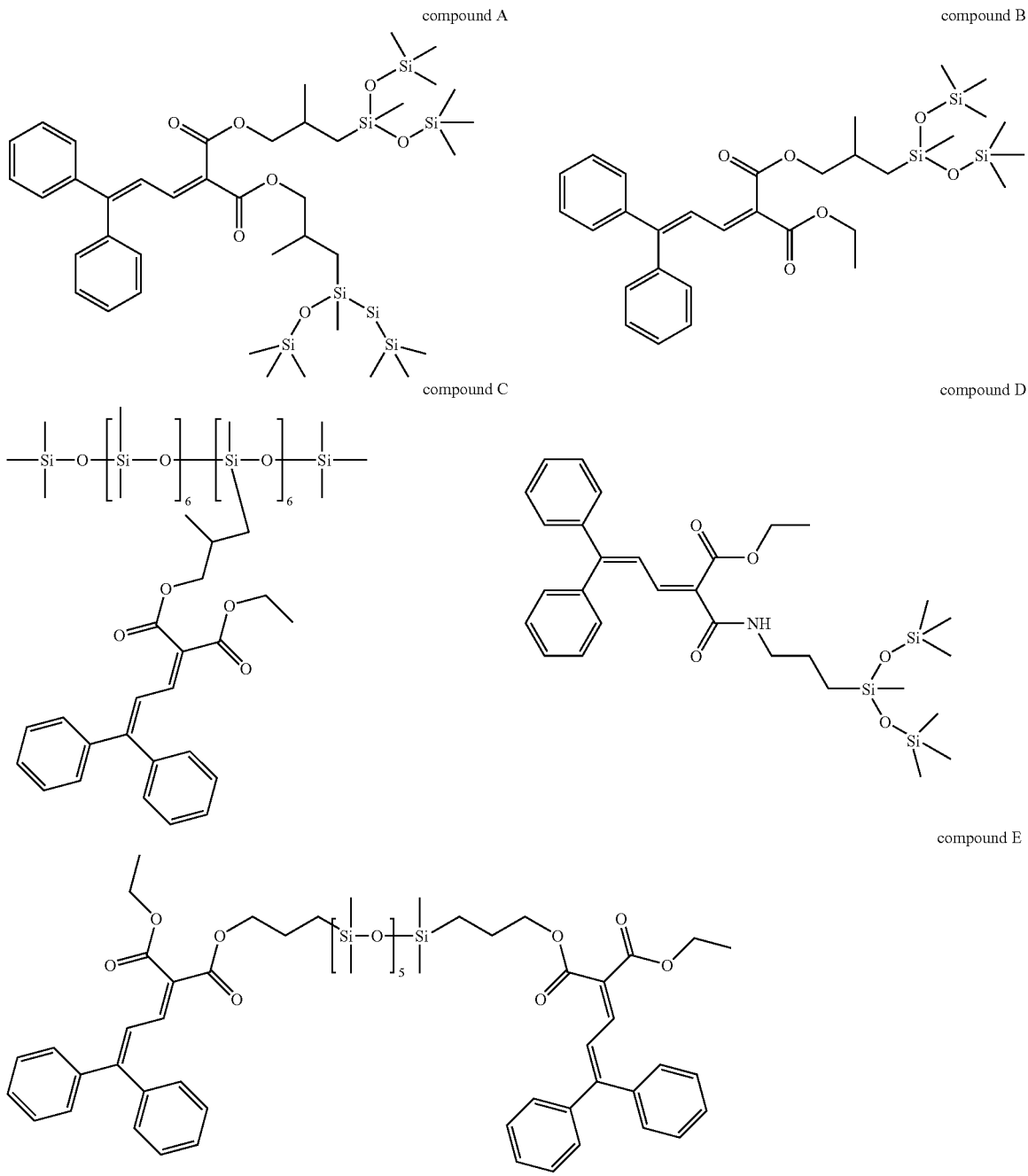

compound A compound B compound C compound D compound E

One family of diorganosiloxane compounds containing a 4,4-diarylbutadiene function of formula (1) or (2) that are particularly preferred are those in which Z is —CN. These particular compounds are effective in the range of long UV-A rays (340-400 nm).

Among these compounds, the ones that are the preferred are those satisfying at least one of the following characteristics and even more preferably all of the following characteristics:

R is $C_1$-$C_4$ alkyl and even more preferably methyl;
B is $C_1$-$C_4$ alkyl and even more preferably methyl (in the case where the compound is of formula (1));
r ranges from 0 to 10 inclusive; s ranges from 0 to 6 inclusive (in the case where the compound is of formula (1));
t+u ranges from 3 to 5 (in the case where the compound is of formula (2));
n is 0;
W is $CH_2$;
p is 1;
Y is H or $CH_3$.

Among these compounds of formula (1), the ones that are even more particularly preferred are the compounds F, G, H, I and J below:

compound F
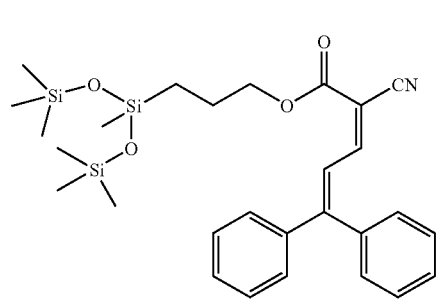
compound G
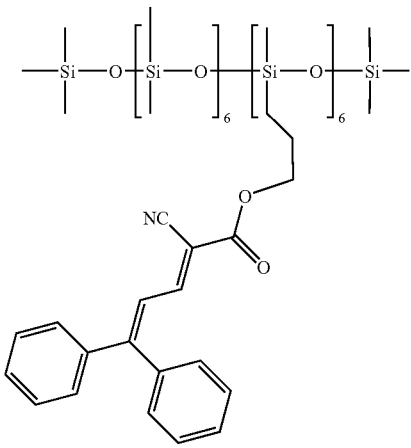
compound H
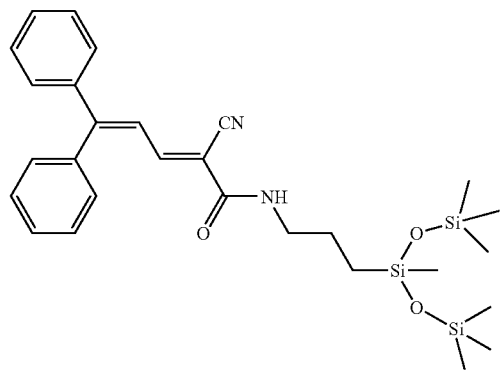
compounds I
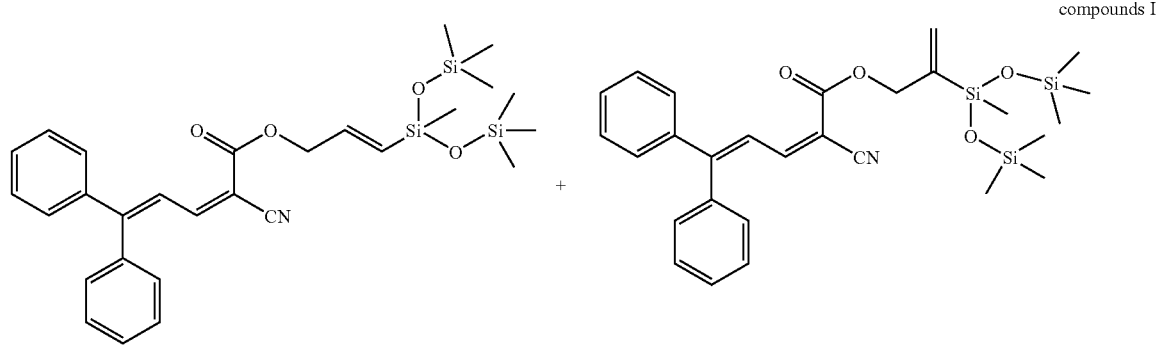
compound J
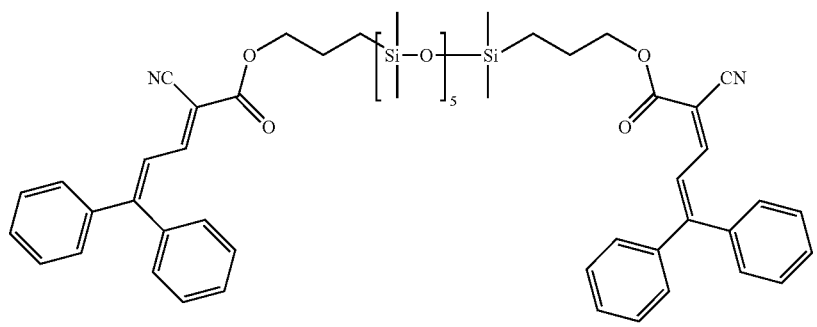

To prepare the derivatives of formula (1) or (2), a conventional process may be performed, by carrying out a hydrosilylation reaction starting with the corresponding siloxane derivative in which, for example, all the radicals A are hydrogen atoms. This derivative is referred to hereinbelow as the SiH-containing derivative and the corresponding synthetic route is referred to as (Route 1).

The SiH groups may be present in the chain and/or at the ends of the chain. These SiH-containing derivatives are products that are well known in the silicone industry and are generally commercially available. They are described, for example, in U.S. Pat. Nos. 3,220,972, 3,697,473 and 4,340,709.

The SiH-containing derivatives corresponding, respectively, to the compounds of formulae (1) and (2) may thus be represented by formulae (4) and (5) below:

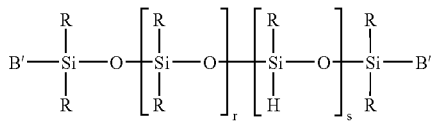

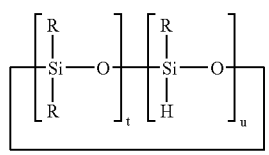

in which:
R, r, s, t and u are as defined above for formulae (1) and (2),
B', which may be identical or different, are each a radical R or a hydrogen atom.

In order to prepare the siloxane compounds of the invention of formula (1) or (2) above, the process is performed in the following manner: (Scheme 1): on the SiH-containing derivative of corresponding formula (4) or (5), a hydrosilylation reaction is performed in the presence of a catalytically effective amount of a platinum catalyst on a 4,4-diarylbutadiene organic derivative of formula (6) below:

Scheme 1

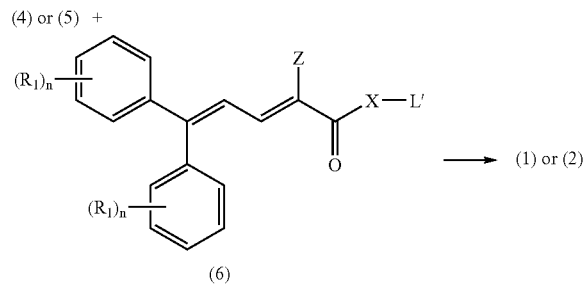

in which $R_1$, Z, X and n have the same meaning as in formula (3) above and L' corresponds to one of the two formulae (b) and (b') below:

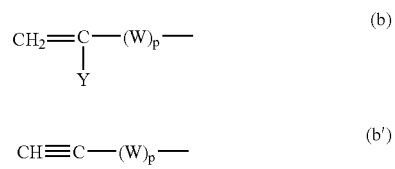

in which Y, W and p have the same meanings as in formulae (a), (a') and (a'') above.

The hydrosilylation reaction is thus performed according to one of the following two reactions:

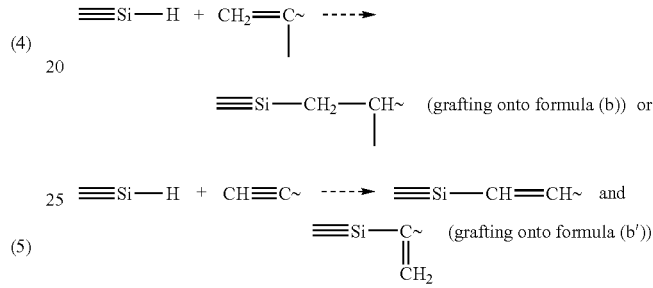

The derivatives of formula (6) are obtained by Knoevenagel condensation of a β-phenylcinnamaldehyde derivative on a derivative of formula (7) as described in EP-916,335:

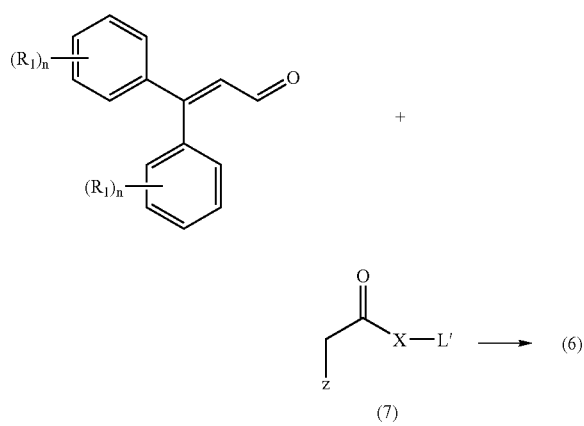

in which the radicals $R_1$, Z, X, L' and n have the same meaning as in formulae (3) and (6) above.

The derivatives of formula (7) are obtained by alkylation of the corresponding acid derivatives with corresponding alkene or alkyne halides.

As derivatives of the type Z-CH$_2$—X-L', mention may be made of diallyl malonate (RN 1797-75-7), allyl cyanoacetate (RN 13361-32-5) or 2-propenyl acetoacetate (RN 1118-84-9), which are commercial products.

In the case of the diorganosiloxane amide derivatives (X represents NR$_3$), another synthetic route (Route 2) for obtaining the compounds of formula (1) or (2) entails reacting a β-phenylcinnamaldehyde derivative with an aminodiorganosiloxane of formula (8) below:

Scheme 2

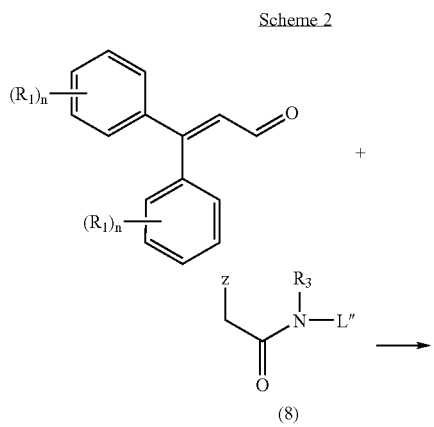

(8)

in which the radicals $R_1$, Z, $R_3$ and n have the same meaning as in the above formulae and L″ corresponds to formula (c) below:

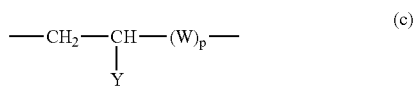

in which Y, W and p have the same meanings as in formula (a) above.

These derivatives (8) may be obtained by condensation of an acid chloride on the amino diorganosiloxanes of formula (9) below:

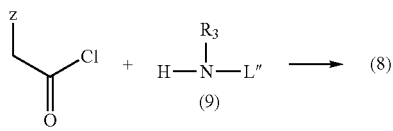

in which Z, $R_3$ and L″ have the same meanings as in the above formulae.

As derivatives of the type Z-$CH_2$—COCl, mention may be made of cyanoacetyl chloride or monoethylmalonic acid chloride, which are commercial products.

The preparation of the aminosiloxanes of formula (9) is described, for example, in GB-185,984. As aminosiloxanes that are particularly suitable for preparing the compounds according to the invention, mention may be made of aminopropylheptamethyltrisiloxane, aminoisobutylheptamethyltrisiloxane or trimethylsilylamodimethicones such as: the product sold under the trademark "X2-8260" by Dow Corning, with an amine number of 2.8 meq/g; the product sold under the trademark "SLM 55051/3" by Wacker, with an amine number of 0.47 meq/g; $C_{12}$ dimethylalkyl PDMSs, such as the product sold under the trademark "SLM 23046/1" by Wacker, with an amine number of 1.2 meq/gram; α,ω-trimethyl polymethyl(fatty)alkyl arylalkylsiloxanes, such as the product sold under the trademark "SLM 23056/2" by Wacker, with an amine number of 1.3 meq/gram; PDMSs in which the $NH_2$ radical is in an α and ω position relative to an alkyl site, such as the products sold under the trademarks "Tegomer A-SI 2120" with an amine number of 1.95 meq/g and "Tegomer A-SI 2320" with an amine number of 0.86 meq/gram, by Goldschmidt.

The preparation of the cyclic aminosiloxanes is described, for example, in the article by A. Kopylov, Zh. Obshch. Khim., 54(2), 367-71 (1984).

The compounds of formula (I) are generally present in the compositions of the invention in proportions of between 0.01% and 20% by weight and preferably between 0.1% and 10% by weight relative to the total weight of the composition.

The compositions in accordance with the invention may also comprise other additional UV-A-active and/or UV-B-active organic or mineral UV-screening agents that are water-soluble, liposoluble or even insoluble in the cosmetic solvents commonly used.

The additional organic screening agents are selected especially from among the anthranilates; cinnamic derivatives; dibenzoylmethane derivatives; salicylic derivatives; camphor derivatives; triazine derivatives such as those described in U.S. Pat. No. 4,367,390, EP-863,145, EP-517,104, EP-570, 838, EP-796,851, EP-775,698, EP-878,469, EP-933,376, EP-507,691, EP-507,692, EP-790,243, EP-944,624; benzophenone derivatives; β,β-diphenylacrylate derivatives; benzotriazole derivatives; benzalmalonate derivatives; benzimidazole derivatives; imidazolines; bis-benzazolyl derivatives as described in EP-669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB-2-303,549, DE-197,26, 184 and EP-893,119; benzoxazole derivatives as described in EP-0-832,642, EP-1-027,883, EP-1-300,137 and DE-101,62, 844; screening polymers and screening silicones other than those of formula (1) or (2) such as those described especially in patent application WO 93/04665; α-alkylstyrene-based dimers, such as those described in DE-198,55,649; non-siliceous 4,4-diarylbutadienes such as those described in EP-0-967,200, DE-197,46,654, DE-197,55,649, EP-A-1-008586, EP-1-133,980 and EP-133,981, and mixtures thereof.

As examples of additional organic screening agents, mention may be made of those denoted hereinbelow under their INCI name:

Para-Aminobenzoic Acid Derivatives:

PABA,

Ethyl PABA,

Ethyl dihydroxypropyl PABA,

Ethylhexyl dimethyl PABA sold in particular under the name "Escalol 507" by ISP, Glyceryl PABA, PEG-25 PABA sold under the name "Uvinul P25" by BASF.

Salicylic Derivatives:

Homosalate sold under the name "Eusolex HMS" by Rona/EM Industries, Ethylhexyl salicylate sold under the name "Neo Heliopan OS" by Haarmann and Reimer, Dipropylene glycol salicylate sold under the name "Dipsal" by Scher, TEA salicylate sold under the name "Neo Heliopan TS" by Haarmann and Reimer.

Dibenzoylmethane Derivatives:

Butyl methoxydibenzoylmethane sold in particular under the trademark "Parsol 1789" by Hoffmann LaRoche, Isopropyldibenzoylmethane.

Cinnamic Derivatives:

Ethylhexyl methoxycinnamate sold in particular under the trademark "Parsol MCX" by Hoffmann LaRoche, Isopropyl methoxycinnamate, Isoamyl methoxycinnamate sold under the trademark "Neo Heliopan E 1000" by Haarmann and Reimer, Cinoxate, DEA methoxycinnamate, Diisopropyl methylcinnamate, Glyceryl ethylhexanoate dimethoxycinnamate.

β,β'-Diphenylacrylate Derivatives:

Octocrylene sold in particular under the trademark "Uvinul N539" by BASF,

Etocrylene sold in particular under the trademark "Uvinul N35" by BASF.

Benzophenone Derivatives:

Benzophenone-1 sold under the trademark "Uvinul 400" by BASF,

Benzophenone-2 sold under the trademark "Uvinul D50" by BASF,

Benzophenone-3 or Oxybenzone sold under the trademark "Uvinul M40" by BASF,

Benzophenone-4 sold under the trademark "Uvinul MS40" by BASF,

Benzophenone-5,

Benzophenone-6 sold under the trademark "Helisorb 11" by Norquay,

Benzophenone-8 sold under the trademark "Spectra-Sorb UV-24" by American Cyanamid, Benzophenone-9 sold under the trademark "Uvinul DS-49" by BASF, Benzophenone-12, n-Hexyl 2-(4-diethylamino-2-hydroxybenzoyl)benzoate.

Benzylidenecamphor Derivatives:

3-Benzylidenecamphor manufactured under the name "Mexoryl SD" by Chimex,

4-Methylbenzylidenecamphor sold under the name "Eusolex 6300" by Merck,

Benzylidenecamphorsulfonic acid manufactured under the name "Mexoryl SL" by Chimex, Camphor benzalkonium methosulfate manufactured under the name "Mexoryl SO" by Chimex, Terephthalylidenedicamphorsulfonic acid manufactured under the name "Mexoryl SX" by Chimex, Polyacrylamidomethylbenzylidenecamphor manufactured under the name "Mexoryl SW" by Chimex.

Phenylbenzimidazole Derivatives:

Phenylbenzimidazolesulfonic acid sold in particular under the trademark "Eusolex 232" by Merck, Disodium phenyl dibenzimidazole tetrasulfonate sold under the trademark "Neo Heliopan AP" by Haarmann and Reimer.

Triazine Derivatives:

Anisotriazine sold under the trademark "Tinosorb S" by Ciba Geigy,

Ethylhexyltriazone sold in particular under the trademark "Uvinul T150" by BASF, Diethylhexylbutamidotriazone sold under the trademark "UV-Asorb HEB" by Sigma 3V.

Phenylbenzotriazole Derivatives:

Drometrizole trisiloxane sold under the name "Silatrizole" by Rhodia Chimie,

Methylenebis(benzotriazolyl)tetramethylbutylphenol sold in solid form under the trademark "Mixxim BB/100" by Fairmount Chemical, or in micronized form as an aqueous dispersion under the trademark "Tinosorb M" by Ciba. Specialty Chemicals.

Anthranilic Derivatives:

Menthyl anthranilate sold under the trademark "Neo Heliopan MA" by Haarmann and Reimer.

Imidazoline Derivatives:

Ethylhexyldimethoxybenzylidenedioxoimidazoline propionate.

Benzmalonate Derivatives:

Polyorganosiloxane containing a benzalmalonate function, such as the product Polysilicone-15 sold under the trademark "Parsol SLX" by Hoffmann LaRoche.

Non-Siliceous 4,4-diarylbutadiene Derivatives:

1,1-Dicarboxy(2,2'-dimethylpropyl)-4,4-diphenylbutadiene.

Benzoxazole Derivatives:

2,4-Bis[5-1 (dimethylpropyl)benzoxazol-2-yl(4-phenyl)imino]-6-(2-ethylhexyl)imino-1,3,5-triazine sold under the name UV-Asorb K2A by Sigma 3V, and mixtures thereof.

The additional organic UV-screening agents that are preferred are:

Ethylhexyl salicylate,

Ethylhexyl methoxycinnamate,

Butyl methoxydibenzoylmethane,

Octocrylene,

Phenylbenzimidazolesulfonic acid,

Benzophenone-3,

Benzophenone-4,

Benzophenone-5, n-Hexyl 2-(4-diethylamino-2-hydroxybenzoyl)benzoate,

4-Methylbenzylidenecamphor,

Terephthalylidenedicamphorsulfonic acid,

Disodium phenyldibenzimidazoletetrasulfonate,

Anisotriazine,

Ethylhexyltriazone,

Diethylhexylbutamidotriazone,

Methylenebis(benzotriazolyl)tetramethylbutylphenol,

Drometrizole trisiloxane,

Polysilicone-15, 1,1-Dicarboxy(2,2'-dimethylpropyl)-4,4-diphenylbutadiene, 2,4-Bis[5-1 (dimethylpropyl)benzoxazol-2-yl(4-phenyl)imino]-6-(2-ethylhexyl)imino-1,3,5-triazine and mixtures thereof.

The additional mineral screening agents are selected from among pigments or even nanopigments (mean size of the primary particles: generally between 5 nm and 100 nm and preferably between 10 nm and 50 nm) of coated or uncoated metal oxides such as, for example, nanopigments of titanium oxide (amorphous or crystallized in rutile and/or anatase form), of iron oxide, of zinc oxide, of zirconium oxide or of cerium oxide and mixtures thereof which are all UV photoprotective agents that are well known per se. Standard coating agents are, moreover, alumina and/or aluminum stearate. Such coated or uncoated metal oxide nanopigments are described in particular in EP-518,772 and EP-518,773.

The additional UV-screening agents in accordance with the invention are generally present in the compositions according to the invention in proportions ranging from 0.01% to 20% by weight relative to the total weight of the composition, and preferably ranging from 0.1% to 10% by weight relative to the total weight of the composition.

The cosmetic compositions according to the invention may also contain agents for artificially tanning and/or browning the skin (self-tanning agents) such as dihydroxyacetone (DHA). They are preferably present in amounts ranging from 0.1% to 10% and more preferably from 0.2% to 8% by weight relative to the total weight of the composition.

The compositions in accordance with the present invention may also comprise standard cosmetic adjuvants selected especially from among fatty substances, organic solvents, ionic or nonionic thickeners, softeners, humectants, antioxidants, moisturizers, desquamating agents, free-radical scavengers, antipollution agents, antibacterial agents, anti-inflammatory agents, depigmenting agents, propigmenting agents, opacifiers, stabilizers, emollients, silicones, antifoams, insect repellents, fragrances, preservatives, anionic, cationic, nonionic, zwitterionic or amphoteric surfactants, substance P antagonists, substance CGRP antagonists, fillers, pigments, polymers, propellants, acidifying or basifying agents, or any other ingredient usually used in cosmetics and/or dermatology.

The fatty substances may be an oil or a wax or mixtures thereof. The term "oil" means a compound that is liquid at room temperature. The term "wax" means a compound that is solid or substantially solid at room temperature, and whose melting point is generally above 35° C.

Oils that may be mentioned include mineral oils (paraffin); plant oils (sweet almond oil, macadamia oil, blackcurrant pip oil or jojoba oil); synthetic oils, for instance perhydrosqualene, fatty alcohols, fatty acids or fatty esters (for instance the $C_{12}$-$C_{15}$ alkyl benzoate sold under the trademark "Finsolv TN" by Witco, octyl palmitate, isopropyl lanolate, triglycerides, including capric/caprylic acid triglycerides, oxyethylenated or oxypropylenated fatty esters and ethers; silicone oils (cyclomethicone and polydimethylsiloxanes or PDMS) or fluoro oils, and polyalkylenes.

Waxy compounds that may be mentioned include paraffin, carnauba wax, beeswax and hydrogenated castor oil.

Among the organic solvents that may be mentioned are lower alcohols and polyols. These lower polyols may be chosen from glycols and glycol ethers, for instance ethylene glycol, propylene glycol, butylene glycol, dipropylene glycol or diethylene glycol.

The thickeners may be chosen especially from among crosslinked acrylic polymers, for instance carbomers, acrylate/$C_{10}$-$C_{30}$ alkylacrylate crosslinked polymers of the type such as Pemulen or polyacrylate-3 sold under the name Viscophobe DB 1000 by Amerchol; polyacrylamides such as the polyacrylamide, $C_{13}$-$C_{14}$ isoparaffin and laureth-7 emulsion sold under the name Sepigel 305 by SEPPIC, AMPS homopolymers or copolymers such as Hostacerin AMPS sold by Clariant, modified or unmodified guar gums and celluloses, such as hydroxypropyl guar gum, methylhydroxyethylcellulose and hydroxypropylmethylcellulose, xanthan gum, and nanometric silicas of the Aerosil type.

Needless to say, one skilled in the art will take care to select the optional additional compound(s) mentioned above and/or the amounts thereof such that the advantageous properties intrinsically associated with the compounds in accordance with the invention are not, or are not substantially, adversely affected by the envisaged addition(s).

The compositions according to the invention may be prepared according to techniques that are well known to those skilled in the art, in particular those intended for the preparation of emulsions of oil-in-water or water-in-oil type.

This composition may be in particular in the form of a simple or complex emulsion (O/W, W/O, O/W/O or W/O/W emulsion) such as a cream or a milk, in the form of a gel or a cream-gel, or in the form of a lotion, an oil, a powder or a solid tube, and may optionally be packaged as an aerosol and may be in the form of a mousse or a spray.

The compositions according to the invention are preferably in the form of an oil-in-water or water-in-oil emulsion.

When it is an emulsion, the aqueous phase of this emulsion may comprise a nonionic vesicular dispersion prepared according to known processes (Bangham, Standish and Watkins, *J. Mol. Biol.*, 13, 238 (1965), FR-2,315,991 and FR-2,416,008).

When the cosmetic composition according to the invention is used to care for the human epidermis, it may be in the form of a suspension or a dispersion in solvents or fatty substances, in the form of a nonionic vesicular dispersion or in the form of an emulsion, preferably of oil-in-water type, such as a cream or a milk, or in the form of an ointment, a gel, a cream-gel, an antisun oil, a solid tube, a powder, an aerosol mousse or a spray.

When the cosmetic composition according to the invention is used for haircare, it may be in the form of a shampoo, a lotion, a gel, an emulsion or a nonionic vesicular dispersion and may constitute, for example, a rinse-out composition, to be applied before or after shampooing, before or after dyeing or bleaching, or before, during or after permanent-waving or relaxing the hair, a styling or treating lotion or gel, a blow-drying or hairsetting lotion or gel, or a composition for permanent-waving, relaxing, dyeing or bleaching the hair.

When the composition is used as a makeup product for the nails, the lips, the eyelashes, the eyebrows or the skin, such as an epidermal treatment cream, a foundation, a tube of lipstick, an eyeshadow, a makeup rouge, a mascara or an eyeliner, it may be in solid or pasty, anhydrous or aqueous form, such as oil-in-water or water-in-oil emulsions, nonionic vesicular dispersions or suspensions.

The present invention also features formulation of a compound of formula (1) or (2) into cosmetic compositions as an agent for controlling the variation in the color of the skin caused by UV-A radiation.

This invention also features the use of a compound of formula (1) as defined above as an agent for photostabilizing synthetic polymers such as plastics or lenses, in particular spectacle lenses or contact lenses.

In order to further illustrate the present invention and the advantages thereof, the following specific examples are given, it being understood that same are intended only as illustrative and in nowise limitative. In said examples to follow, all parts and percentages are given by weight, unless otherwise indicated.

PREPARATION EXAMPLES

Example 1

Preparation of monoethyl mono-3-[1,3,3,3-tetramethyl-1-[(trimethylsilyl)oxy]disiloxanyl]-2-methylpropyl 2-(3,3-diphenylprop-2-enylene)malonate (via Route 1)

Compound B

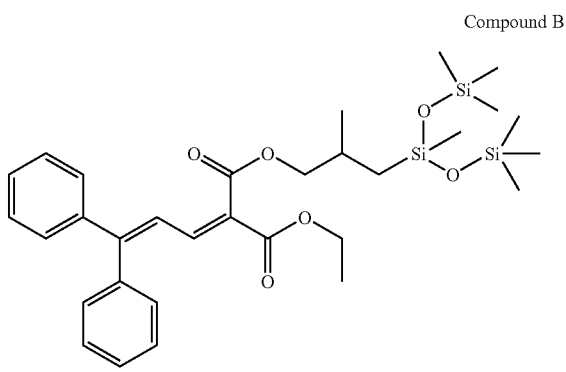

First Step: Preparation of Monoethyl Monomethallyl Malonate

A mixture of the potassium salt of monoethyl malonic acid (17 g, 0.1 mol) and methallyl chloride (9.8 ml, 0.1 mol) in 150 ml of DMF is maintained at 50° C. for four hours in a reactor. The mineral salts are filtered off on a sinter funnel and the DMF is evaporated off under reduced pressure. The mixture is taken up in 100 ml of ethyl acetate. The organic phase is washed three times with water. The organic phase is dried over sodium sulfate and concentrated under reduced pressure. 16 g of a pale yellow oil are obtained, and are purified by fractional distillation. The fractions distilling at 58° C. under a vacuum of 0.1 hPa are recovered in the form of a colorless oil (8 g, 40% yield) of monoethyl monomethallyl malonate, which is used without further purification in the following step.

Second Step: Preparation of monoethyl monomethallyl 2-(3,3-diphenylprop-2-enylene)malonate β-Phenylcinnamaldehyde (2 g, 0.0096 mol) is dissolved in 50 ml of isopropanol in a reactor. 0.24 ml of the piperidine and the derivative from the first step (1.97 g, 0.011 mol) are added thereto. The reaction mixture is heated at 60° C. for 2 hours 30 minutes. The isopropanol is removed under reduced pressure. After crystallization from heptane, the derivative monoethyl monomethallyl 2-(3,3-diphenylprop-2-enylene)malonate (2.05 g, 57% yield) is obtained in the form of a pale yellow powder:

$^1$H NMR (400 MHz): presence of the two E, Z isomers in a 4:1 ratio.

m.p. 95° C.

Third Step: Preparation of the Derivative of Example 1

A solution of the above product (1 g, 0.0026 mol) and of catalyst (complex containing 3-3.5% by weight of Pt in cyclovinylmethylsiloxane from Hüls Petrarch PC085: 40 µl) in 30 ml of toluene is heated to 80° C. 0.65 g (0.029 mol) of heptamethyltrisiloxane is added dropwise thereto over 20 minutes. The solvent is evaporated off under vacuum. The oil obtained is purified by chromatography on a column of silica (eluent: CH$_2$Cl$_2$/heptane). The clean fractions of the derivative of Example 1 are recovered (0.5 g, 31% yield) in the form of a pale yellow oil:

$^1$H NMR (400 MHz): presence of the two E, Z isomers in a 4:1 ratio.

UV (Ethanol) $\lambda_{max}$=333 nm, $\epsilon_{max}$=39 530 E1%=660

Example 2

Preparation of the Random Derivative of Formula (1): s=6, r=6, B=CH$_3$, R=CH$_3$, n=0, Z=—COOEt, X=O, L of Formula (a): Y=CH$_3$, p=1, W=CH$_2$ (Via Route 1):

Compound C

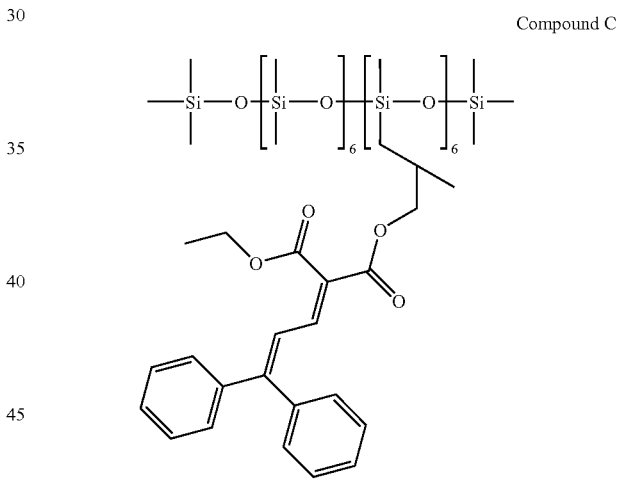

A solution of the above product (1 g, 0.0026 mol) and of catalyst (complex containing 3-3.5% by weight of Pt in cyclovinylmethylsiloxane from Hüls Petrarch PC085: 40 µl) in 30 ml of toluene is heated to 90° C. 0.42 g (2.5 meq of SiH) of random copolymer (50-55%) methylhydro—(45-50%) dimethylsiloxane (PS122.5 from Petrarch) is added thereto. The mixture is heated at 90° C. until the band at 2180 cm$^{-1}$ in infrared has disappeared (i.e., ten hours). The solvent is evaporated off under vacuum. The oil obtained is washed twice with 80% ethanol. The pale yellow oil obtained is taken up in dichloromethane, dried over sodium sulfate and passed through a bed of silica. After evaporating off the solvent, clean fractions of the derivative of Example 2 (0.8 g, 56% yield) are obtained in the form of a pale yellow oil:

UV (Ethanol) $\lambda_{max}$=333 nm E1%=590.

Example 3

Preparation of 3-[1,3,3,3-tetramethyl-1-[(trimethylsilyl)oxy]disiloxanyl]propyl 2-cyano-5,5-diphenyl-penta-2,4-dienoate (via Route 1)

Compound E

First Step: Preparation of allyl 2-cyano-5,5-diphenylpenta-2,4-dienepentanoate β-Phenylcinnamaldehyde (4 g, 0.0192 mol) is dissolved in 100 ml of isopropanol in a reactor. 0.5 ml of piperidine and allyl cyanoacetate (2.64 g, 0.021 mol) are added thereto. The reaction mixture is heated at 60° C. for 2 hours 30 minutes. The solution is concentrated under reduced pressure. The excess malonate is removed by distillation under a vacuum of 0.02 hPa. After purification by chromatography on a column of silica (eluent: 95/5 heptane/EtOAc), clean fractions of the derivative allyl 2-cyano-5,5-diphenylpenta-2,4-dienepentanoate (2.34 g, 77% yield) are obtained in the form of a pale yellow powder, which is used without further purification in the following step.

Second Step: Preparation of the Derivative of Example 3

A solution of the above product (1 g, 0.00317 mol) and of catalyst (complex containing 3-3.5% by weight of Pt in cyclo-vinylmethylsiloxane from Hüls Petrarch PC085: 40 μl) in 30 ml of toluene is heated to 80° C. 0.776 g (0.0349 mol) of heptamethyltrisiloxane is added dropwise thereto over 20 minutes. The mixture is heated at 80° C. for 20 hours. The solvent is evaporated off under vacuum. The oil obtained is purified by chromatography on a column of silica (eluent: $CH_2Cl_2$/heptane). The clean fractions of the derivative of Example 3 are recovered (0.93 g, 55% yield) in the form of a pale yellow oil:

UV (Ethanol) $\lambda_{max}$=358 nm, $\epsilon_{max}$=30 874 E1%=574

Example 4

Preparation of the Random Derivative of Formula (1): s=6, r=6, B=$CH_3$, R=$CH_3$, n=0, Z=—CN, X=O, L of Formula (a): Y=H, p=1, W=$CH_2$ (Via Route 1)

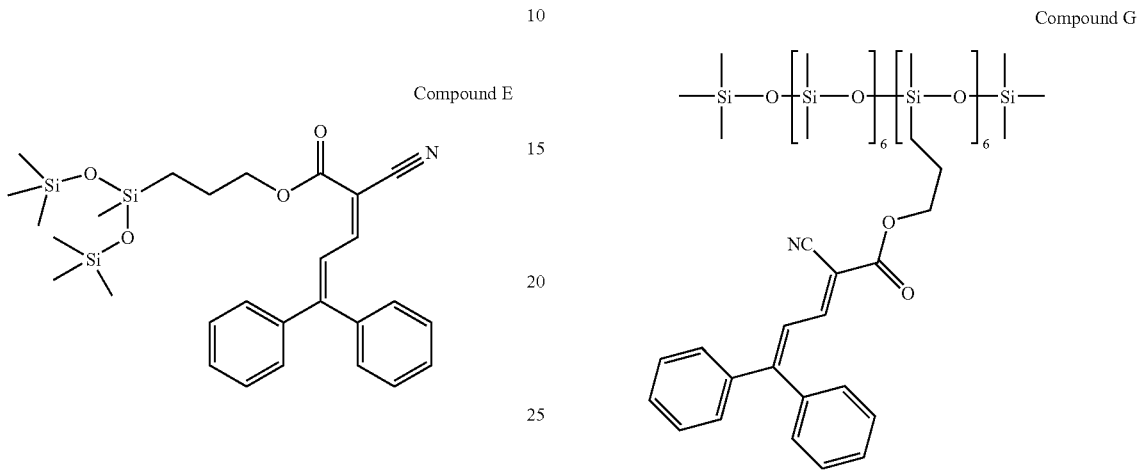

Compound G

A solution of the above product (1 g, 0.00317 mol) and of catalyst (complex containing 3-3.5% by weight of Pt in cyclo-vinylmethylsiloxane from Hüls Petrarch PC085: 40 μl) in 30 ml of toluene is heated to 90° C. 0.52 g (3.1 meq of SiH) of the random copolymer (50-55%) methylhydro—(45-50%) dimethylsiloxane (PS122.5 from Petrarch) is added thereto. The mixture is heated at 90° C. until the band at 2180 $cm^{-1}$ in infrared has disappeared (i.e., 12 hours). The solvent is evaporated off under vacuum. The oil obtained is washed twice with 80% ethanol. The pale yellow oil obtained is taken up in dichloromethane, dried over sodium sulfate and passed through a bed of silica. After evaporating off the solvent, the clean fractions of the derivative of Example 4 (1.06 g, 62% yield) are obtained in the form of a pale yellow oil:

UV (Ethanol) $\lambda_{max}$=359 nm, E1%=660.

Example 5

Preparation of N-[3-[1,3,3,3-tetramethyl-1-[(trimethylsilyl)oxy]disiloxanyl]propyl]-2-cyano-5,6-diphenylpenta-2,4-dienamide (via Route 2)

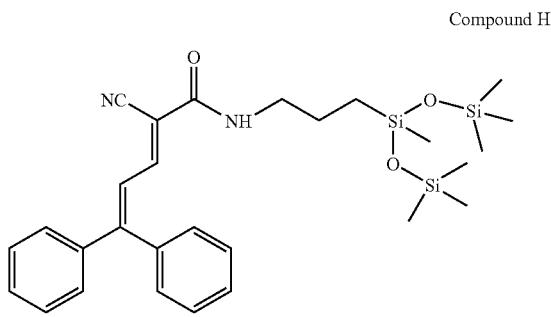

Compound H

First Step: Preparation of cyano-N-[3-[1,3,3,3-tetramethyl-1-[(trimethylsilyl)oxy]disiloxanyl]propyl]acetamide Cyanoacetyl chloride (5.2 g, 0.05 mol) is added dropwise over 20 minutes to a mixture of 3-[1,3,3,3-tetramethyl-1-[(trimethylsilyl)oxy]disiloxanyl]propylamine (13.93 g, 0.05 mol) and of triethylamine (5 g, 0.05 mol) in 40 ml of dichloromethane. The temperature rises to 32° C. The mixture is refluxed for two hours. The reaction mixture is poured into 150 ml of water and is extracted with dichloromethane. The organic phases are washed with water and dried over sodium sulfate, and the solvent is then evaporated off. After purification by passing through a column of silica (eluent: 70/30 heptane/ethyl acetate), 12.2 g (70% yield) of cyano-N-[3-[1,3,3,3-tetramethyl-1-[(trimethylsilyl)oxy]disiloxanyl]propyl]acetamide are obtained in the form of a colorless oil, which is used without further purification in the following step.

Second Step: Preparation of the Derivative of Example 5

β-Phenylcinnamaldehyde (0.6 g, 2.88×10⁻³ mol) is dissolved in 30 ml of isopropanol in a reactor. 0.1 ml of piperidine and the derivative from the preceding step (1 g, 2.88×10⁻³ mol) are added thereto. The reaction mixture is heated at 50° C. for 1 hour 30 minutes. The solution is concentrated under reduced pressure. After purification by chromatography on a column of silica (eluent: 90/10 heptane/EtOAc), the clean fractions of the derivative of the example (0.95 g, 61% yield) are obtained in the form of a pale yellow oil:

UV (Ethanol) $\lambda_{max}$=351 nm, $\epsilon_{max}$=27 650, E1%=515.

Example 6

Preparation of [2-methyl-3-[1,3,3,3-tetramethyl-1-[(trimethylsilyl)oxy]disiloxanyl]-2-methylpropyl 2-(3,3-diphenylprop-2-enylene)malonate (via Route 1)

Compound A

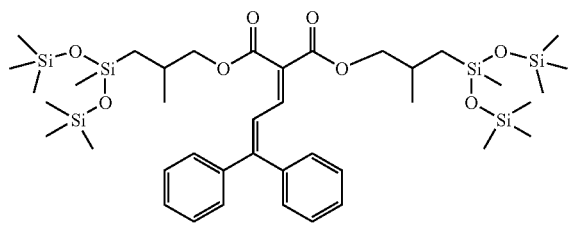

First Step: Preparation of 2-methyl-3-[1,3,3,3-tetramethyl-1-[(trimethylsilyl)oxy]disiloxanyl]propyl malonate A solution of dimethylallyl malonate (10 g, 0.047 mol) and of catalyst (complex containing 3-3.5% by weight of Pt in cyclovinylmethylsiloxane from Hüls Petrarch PC085: 200 μl) in 30 ml of toluene is heated to 80° C. 23 g (0.104 mol) of heptamethyltrisiloxane are added dropwise thereto over 20 minutes. The mixture is heated at 80° C. for 16 hours. The solvent and the excess heptamethyltrisiloxane are evaporated off under vacuum. Bis[2-methyl-3-[1,3,3,3-tetramethyl-1-[(trimethylsilyl)oxy]disiloxanyl]propyl]malonate is thus obtained in the form of an oil, which is used without further purification for the following step.

Second Step: Preparation of the Derivative of Example 6

A mixture of the above derivative (1 g, 0.00234 mol) and of β-phenylcinnamaldehyde (0.487 g, 0.00234 mol) in 20 ml of toluene, in the presence of 0.1 ml of piperidine and 0.06 ml of acetic acid, is refluxed for 12 hours. The reaction mixture is concentrated and the residue is chromatographed on silica (eluent: 50/50 heptane/CH₂Cl₂) to give 0.62 g of the derivative of Example 6 (yield: 32%) in the form of a pale yellow oil:

UV (Ethanol) $\lambda_{max}$=330 nm, $\epsilon_{max}$=28 650, E1%=346.

Example 7

Preparation of ethyl 4,4-diphenyl-1,3-diene-N-[3-[1,3,3,3-tetramethyl-1-[(trimethylsilyl)oxy]disiloxanyl]propyl]-2-(4,4-diphenylprop-2-ethylene)malonamide (via Route 2)

Compound D

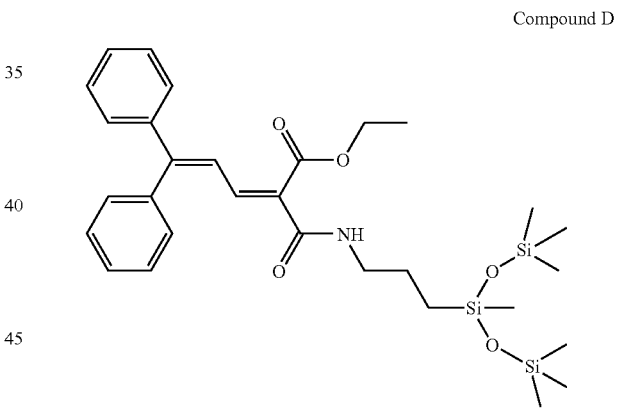

First Step: Preparation of ethyl N-[3-[1,3,3,3-tetramethyl-1-[(trimethylsilyl)oxy]disiloxanyl]propyl]malonamide Malonic acid monoethyl ester chloride (3.3 g, 0.025 mol) is added dropwise at 10° C. over 30 minutes to a mixture of 3-[1,3,3,3-tetramethyl-1-[(trimethylsilyl)oxy]disiloxanyl]propylamine (6.99 g, 0.025 mol) and of triethylamine (2.2 g, 0.0275 mol) in 20 ml of dichloromethane. The reaction mixture is allowed to warm to room temperature and is refluxed for two hours. The reaction mixture is poured into 40 ml of water and is extracted with dichloromethane. The organic phases are washed with water and dried over sodium sulfate, and the solvent is then evaporated off. After purification by passing through a column of silica (eluent: 95/5 CH₂Cl₂/methanol), 2.1 g of a colorless oil are obtained, and are used without further purification in the following step.

Second Step: Preparation of the Derivative of Example 7

A mixture of the above derivative (1 g, 2.54×10⁻³ mol) and of β-phenylcinnamaldehyde (0.53 g, 2.54×10⁻³ mol) is dissolved in 30 ml of isopropyl alcohol, in the presence of 0.1 ml of piperidine, and is maintained at 50° C. for three hours. The reaction mixture is concentrated and the residue is chromatographed on silica (eluent: 80/20 heptane/ethyl acetate) to give 1.22 g (82% yield) of the derivative of Example 7 in the form of a pale yellow oil:

UV (Ethanol) $\lambda_{max}$=335 nm, $\epsilon_{max}$=31 650, E1%=542.

COMPOSITION EXAMPLES

Composition A:

| Phase | Constituents | Concentration (g %) |
|---|---|---|
| A | Glyceryl monostearate/polyethylene glycol stearate (100 EO) mixture (Arlacel 165 - Uniqema) | 1 |
|   | Fatty acids of plant origin (Stearine TP 1200 - Stéarineries Dubois) | 1.5 |
|   | Dimethicone (Dow Corning 200 Fluid 350 CS - Dow Corning) | 0.5 |
|   | Cetyl alcohol (Lanette 16 - Cognis) | 0.5 |
|   | Cetylstearylglucoside/cetylstearyl alcohol mixture (Montanov 68 - SEPPIC) | 2 |
|   | $C_{12}$-$C_{15}$ alkyl benzoate (Finsolv TN - Witco) | 10 |
|   | Compound of Example 1 | 5 |
| B | Glycerol (Pricerine 9091 - Uniqema) | 5 |
|   | Hexadecyl phosphate, potassium salts (Amphisol K - Roche Vitamins) | 1 |
|   | EDTA | 0.1 |
| C | Xanthan gum (Keltrol T - CP Kelco) | 0.2 |
|   | Acrylates/$C_{10}$-$C_{30}$-alkylacrylate crosslinked copolymer (Pemulen TR-1 - Noveon) | 0.2 |
|   | Isohexadecane (Isohexadecane - BP) | 1 |
|   | Triethanolamine | qs pH |
|   | Preservatives | qs |
|   | Demineralized water | qs 100 g |

Laboratory Manufacturing Protocol:

The fatty phase (A) is weighed out and heated on a water bath at 70° C. The aqueous phase (B) is weighed out in the final beaker and heated on a water bath at 70° C. The fatty phase is dispersed in the aqueous phase with stirring using a Moritz rotor/stator stirrer (about 1000 rpm). The mixture of thickeners (C) is incorporated and the resulting mixture is allowed to cool to room temperature with stirring. At about 30° C., the formulation is neutralized and packaged.

Composition B:

| Phase | Constituents | Concentration (g %) |
|---|---|---|
| A | Glyceryl monostearate/polyethylene glycol stearate (100 EO) mixture (Arlacel 165 - Uniqema) | 1 |
|   | Fatty acids of plant origin (Stearine TP 1200 - Stéarineries Dubois) | 1.5 |
|   | Dimethicone (Dow Corning 200 Fluid 350 CS - Dow Corning) | 0.5 |
|   | Cetyl alcohol (Lanette 16 - Cognis) | 0.5 |
|   | Cetylstearylglucoside/cetylstearyl alcohol mixture (Montanov 68 - SEPPIC) | 2 |
|   | $C_{12}$-$C_{15}$ alkyl benzoate (Finsolv TN - Witco) | 10 |
|   | Compound of Example 3 | 5 |
| B | Glycerol (Pricerine 9091 - Uniqema) | 5 |
|   | Hexadecyl phosphate, potassium salts (Amphisol K - Roche Vitamins) | 1 |
|   | EDTA | 0.1 |
| C | Xanthan gum (Keltrol T - CP Kelco) | 0.2 |
|   | Acrylates/$C_{10}$-$C_{30}$-alkylacrylate crosslinked copolymer (Pemulen TR-1 - Noveon) | 0.2 |
|   | Isohexadecane (Isohexadecane - BP) | 1 |
|   | Triethanolamine | qs pH |
|   | Preservatives | qs |
|   | Demineralized water | qs 100 g |

Laboratory Manufacturing Protocol:

The fatty phase (A) is weighed out and heated on a water bath at 70° C. The aqueous phase (B) is weighed out in the final beaker and heated on a water bath at 70° C. The fatty phase is dispersed in the aqueous phase with stirring using a Moritz rotor/stator stirrer (about 1000 rpm). The mixture of thickeners (C) is incorporated and the resulting mixture is allowed to cool to room temperature with stirring. At about 30° C., the formulation is neutralized and packaged.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

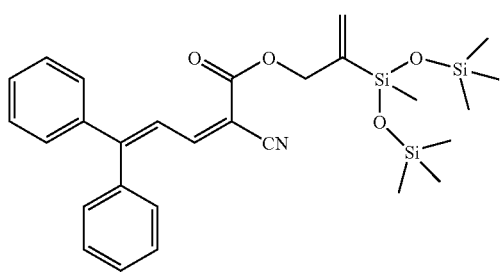

27. The 4,4-diarylbutadiene-substituted diorganopolysiloxane as defined by claim 1, having the structural formula of compound J:
compound J
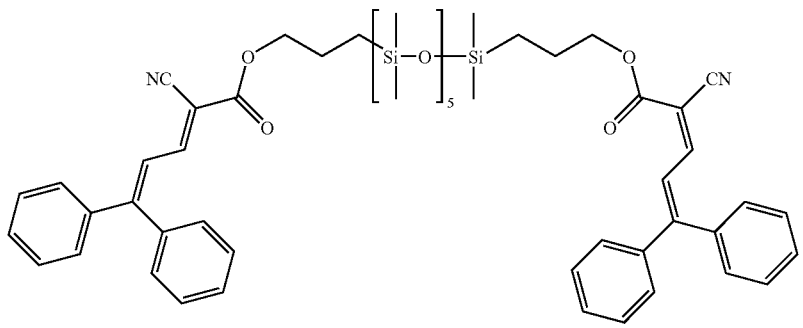

What is claimed is:

1. A 4,4-diarylbutadiene-substituted diorganopolysiloxane having the structural formulae (1) or (2):

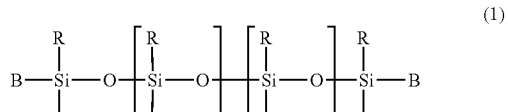

(1)

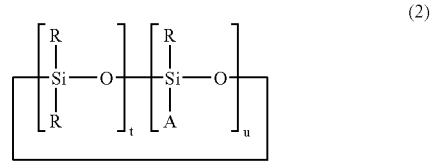

(2)

in which A is a radical of formula (3) below:

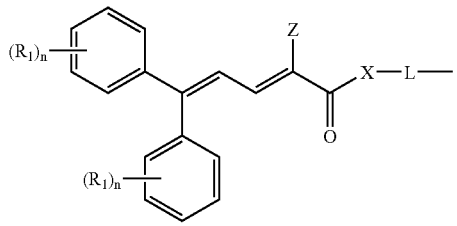

(3)

in which the radicals $R_1$, which may be identical or different, are each a hydroxyl radical, a saturated or unsaturated, linear or branched $C_1$-$C_{10}$ alkyl radical, a saturated or unsaturated, linear or branched $C_1$-$C_{10}$ alkoxy radical, with the proviso that two adjacent groups $R_1$ may together form a $C_1$-$C_3$ alkylenedioxy ring; n is an integer ranging from 0 to 2; the radical Z is hydrogen, —(C=O)$OR_2$, —(C=O)$R_3$, —(C=O)$NR_4R_5$, —$SO_2R_6$, —CN or —(C=O)—X-L; X is —O— or —$NR_4$—; L is a divalent radical attaching the radical A to the silicone chain and corresponding to one of the formulae (a), (a') or (a") below:

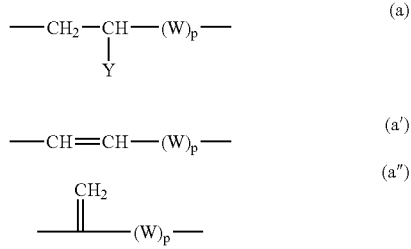

in which W is a saturated or unsaturated, linear or branched $C_1C_6$ alkylene radical, optionally substituted with a hydroxyl radical or a saturated or unsaturated, linear or branched $C_1$-$C_8$ alkyl radical; Y is a hydrogen atom, a hydroxyl radical or a saturated or unsaturated, linear or branched $C_1$-$C_8$ alkyl radical; p is 0 or 1; the radicals R, which may be identical or different, are each a saturated or unsaturated, linear or branched $C_1$-$C_{20}$ alkyl radical, a phenyl radical, a 3,3,3-trifluoropropyl radical or a trimethylsilyloxy radical, at least 80% in numerical terms of the radicals R being methyl radicals; the radicals B, which may be identical or different, are each a radical R or a radical A; r is a number ranging from 0 to 50; s is a number ranging from 0 to 20 and if s is 0, at least one of the two radicals B is a radical A; u is a number ranging from 1 to 6 inclusive; t is a number ranging from 0 to 10; t +u is greater than or equal to 3; the radical $R_2$ is hydrogen or a saturated or unsaturated, linear or branched $C_1$-$C_{20}$ alkyl radical; the radical $R_3$ is a saturated or unsaturated, linear or branched $C_1$-$C_{20}$ alkyl radical or a $C_6$-$C_{12}$ aryl radical; the radicals $R_4$ and $R_5$, which may be identical or different, are each hydrogen or a saturated or unsaturated, linear or branched $C_1$-$C_{20}$ alkyl radical; and the radical $R_6$ is a saturated or unsaturated, linear or branched $C_1$-$C_{20}$ alkyl radical or a $C_6$-$C_{12}$ aryl radical, with the proviso that when two groups (C=O)—X-L- are present, L is bonded to only one group A or B of formula (1) or (2), or mixture thereof.

2. The 4,4-diarylbutadiene-substituted diorganopolysiloxane as defined by claim 1, having the structural formula (1).

3. The 4,4-diarylbutadiene-substituted diorganopolysiloxane as defined by claim 1, having the structural formula (2).

4. The 4,4-diarylbutadiene-substituted diorganopolysiloxane as defined by claim 1, wherein formula (3), Z is a hydrogen atom.

5. The 4,4-diarylbutadiene-substituted diorganopolysiloxane as defined by claim 1, wherein formula (3), Z is —(C=O)$R_2$.

6. The 4,4-diarylbutadiene-substituted diorganopolysiloxane as defined by claim 1, wherein formula (3), Z is —(C=O)$R_3$.

7. The 4,4-diarylbutadiene-substituted diorganopolysiloxane as defined by claim 1, wherein formula (3), Z is —(C=O)$NR_4R_5$.

8. The 4,4-diarylbutadiene-substituted diorganopolysiloxane as defined by claim 1, wherein formula (3), Z is —$SO_2R_6$.

9. The 4,4-diarylbutadiene-substituted diorganopolysiloxane as defined by claim 1, wherein formula (3), Z is —CN.

10. The 4,4-diarylbutadiene-substituted diorganopolysiloxane as defined by claim 1, wherein formula (3), Z is —(C=O)—X-L-.

11. The 4,4-diarylbutadiene-substituted diorganopolysiloxane as defined by claim 1, wherein formula (3), X is —O—.

12. The 4,4-diarylbutadene-substituted diorganopolysiloxane as defined by claim 1, wherein formula (3), X is —$NR_4$—.

13. The 4,4-diarylbutadiene-substituted diorganopolysiloxane as defined by claim 1, wherein formula (3), L is a divalent radical.

14. The 4,4-diarylbutadiene-substituted diorganopolysiloxane as defined by claim 1, wherein formula (3), L is a divalent radical (a').

15. The 4,4-diarylbutadiene-substituted diorganopolysiloxane as defined by claim 1, wherein formula (3), L is a divalent radical (a").

16. The 4,4-diarylbutadiene-substituted diorganopolysiloxane as defined by claim 1, wherein formula (1) or (2) and (3):

the radical Z is —(C=O)$R_3$, —CN or —(C=O)—X-L-;
$R_3$ is a $C_1$-$C_4$ alkyl radical;
R is a $C_1$-$C_4$ alkyl radical;
B is a $C_1$-$C_4$ alkyl radical;
r ranges from 0 to 10 inclusive; s ranges from 0 to 6 inclusive;
t +u ranges from 3 to 5;
n is 0;
W is $CH_2$;
p is 1;
Y is H or $CH_3$.

17. The 4,4-diarylbutadiene-substituted diorganopolysiloxane as defined by claim 1, having the structural formula of compound A:

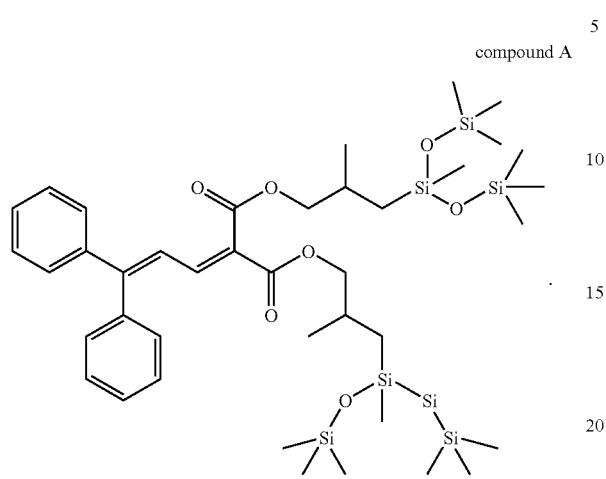
compound A

18. The 4,4-diarylbutadiene-substituted diorganopolysiloxane as defined by claim 1, having the structural formula of compound B:

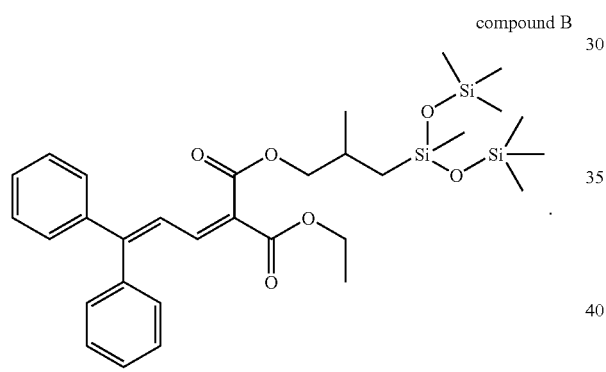
compound B

19. The 4,4-diarylbutadiene-substituted diorganopolysiloxane as defined by claim 1, having the structural formula of compound C:

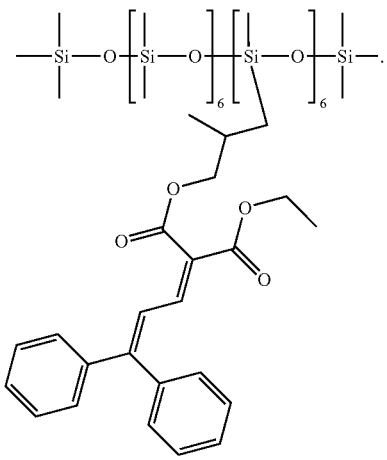
compound C

20. The 4,4-diarylbutadiene-substituted diorganopolysiloxane as defined by claim 1, having the structural formula of compound D:

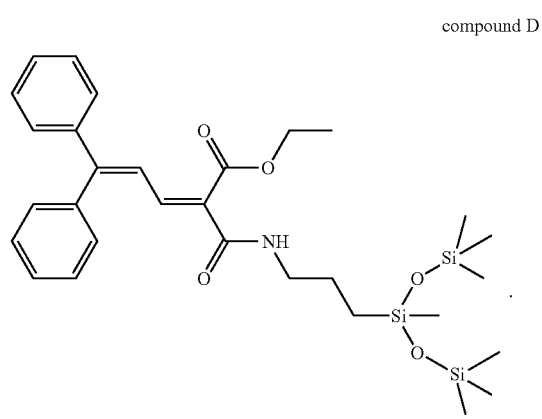
compound D

21. The 4,4-diarylbutadiene-substituted diorganopolysiloxane as defined by claim 1, having the structural formula of compound E:

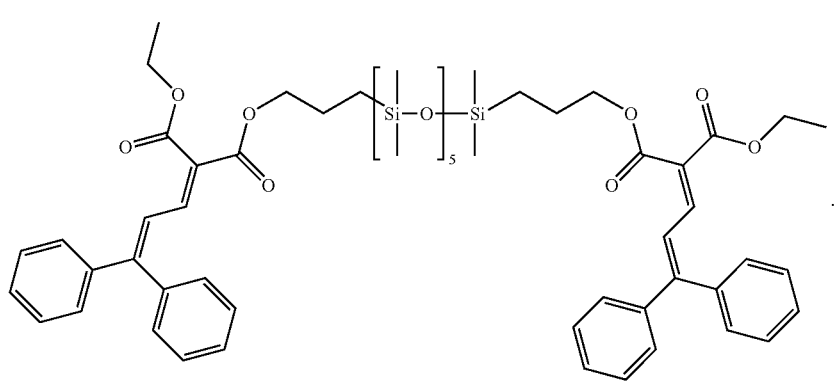
compound E

22. The 4,4-diarylbutadiene-substituted diorganopolysiloxane as defined by claim 9, wherein formula (1) or (2) and (3):

R is a $C_1$-$C_4$ alkyl radical;

B is a $C_1$-$C_4$ alkyl radical;

r ranges from 0 to 10 inclusive; s ranges from 0 to 6 inclusive;

t +u ranges from 3 to 5;

n is 0,

W is $CH_2$, p is 1,

Y is H or $CH_3$ .

23. The 4,4-diarylbutadiene-substituted diorganopolysiloxane as defined by claim 1, having the structural formula of compound F:

Compound F

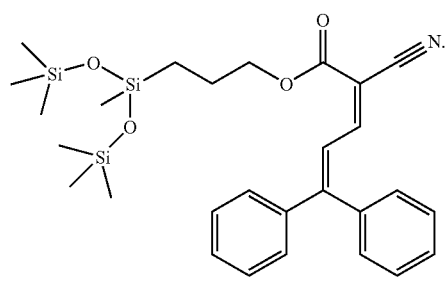

24. The 4,4-diarylbutadiene-substituted diorganopolysiloxane as defined by claim 1, having the structural formula of compound G:

compound G

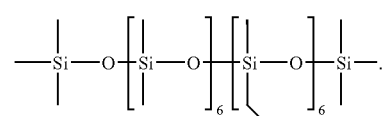

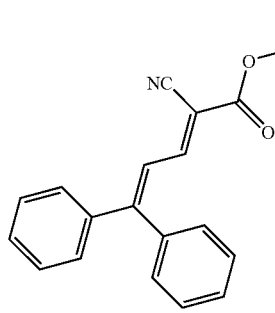

25. The 4,4-diarylbutadiene-substituted diorganopolysiloxane as defined by claim 1, having the structural formula of compound H:

compound H

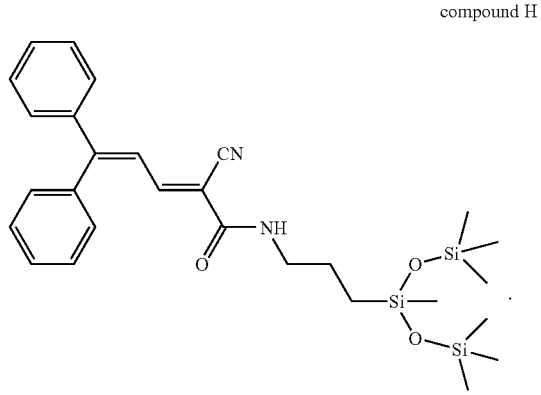

26. The 4,4-diarylbutadiene-substituted diorganopolysiloxane as defined by claim 1, having the structural formula of the mixture of compounds I:

compounds I

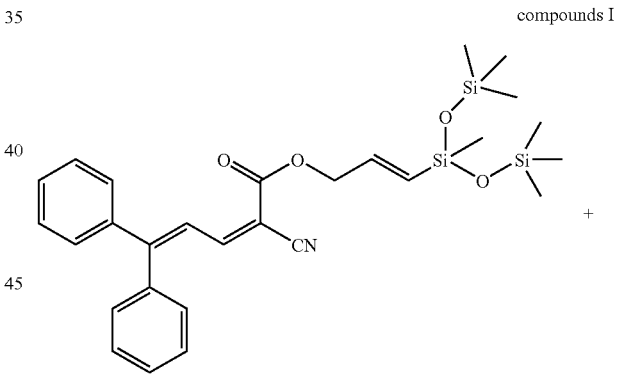

+